(12) United States Patent
Aiba et al.

(10) Patent No.: US 8,394,615 B2
(45) Date of Patent: Mar. 12, 2013

(54) GLUCOSE DEHYDROGENASE

(75) Inventors: Hiroshi Aiba, Tsuruga (JP); Yoshiaki Nishiya, Tsuruga (JP); Tadayuki Imanaka, Kyoto (JP); Haruyuki Atomi, Kyoto (JP)

(73) Assignees: Toyo Boseki Kabushiki Kaisha, Osaka-shi (JP); Kyoto University, Kyoto-shi (JP)

( * ) Notice: Subject to any disclaimer, the term of this patent is extended or adjusted under 35 U.S.C. 154(b) by 280 days.

(21) Appl. No.: 12/811,735

(22) PCT Filed: Dec. 26, 2008

(86) PCT No.: PCT/JP2008/073749
§ 371 (c)(1),
(2), (4) Date: Sep. 21, 2010

(87) PCT Pub. No.: WO2009/087929
PCT Pub. Date: Jul. 16, 2009

(65) Prior Publication Data
US 2011/0020851 A1    Jan. 27, 2011

(30) Foreign Application Priority Data

Jan. 7, 2008  (JP) ................. 2008-000677
Mar. 10, 2008  (JP) ................. 2008-060032

(51) Int. Cl.
C12N 9/04 (2006.01)
C12N 1/20 (2006.01)
C12N 15/00 (2006.01)
C12Q 1/54 (2006.01)
C07H 21/04 (2006.01)
C07K 1/00 (2006.01)

(52) U.S. Cl. ............ 435/190; 435/14; 435/252.33; 435/252.3; 435/320.1; 536/23.2; 536/23.1; 530/350

(58) Field of Classification Search .......... 435/190, 435/14, 252.33, 252.3, 320.1; 536/23.2, 536/23.1; 530/350
See application file for complete search history.

(56) References Cited

U.S. PATENT DOCUMENTS 7,005,048 B1 * 2/2006 Watanabe et al. ...... 204/403.14
2002/0037564 A1    3/2002 Blum

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Siebers et al., Reconstruction of the central carbohydrate metabolism of *Thermoproteus tenax* by use of genomic and biochemical data. J. Bacteriol., 2004, vol. 186 (7): 2179-2194.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Giardina et al., *Biochem. J.*, 239(3): 517-522 (1986).
Siebers et al., *Arch. Microbiol.*, 168(2): 120-127 (1997).
Smith et al., *Biochem. J.*, 261(3): 973-977 (1989).
Bright et al., *European Journal of Biochemistry*, 211(3): 549-554 (1993).
Lamble et al., *The Journal of Biological Chemistry*, 278(36): 34066-34072 (Sep. 5, 2003).
Niehaus et al., *Applied Microbiology and Biotechnology*, 51(6): 711-729 (1999).
Schiraldi et al., *Archaea*, 1(2): 75-86 (2002).
Van Den Burg, Bertus, *Current Opinion in Microbiology*, 6(3): 213-218 (2003).
European Patent Office, Supplementary European Search Report in European Patent Application No. 08 86 9662 (Aug. 19, 2011).
Japanese Patent Office, International Search Report in International Patent Application PCT/JP2008/073749 (Jan. 27, 2009), English translation.

* cited by examiner

*Primary Examiner* — Ganapathirama Raghu
(74) *Attorney, Agent, or Firm* — Leydig, Voit & Mayer, Ltd.

(57) ABSTRACT

The invention provides a glucose dehydrogenase that is an extremely stable enzyme having a thermostability of 80° C. or more, and that does not substantially act upon saccharides other than glucose (e.g., having a reactivity of less than 3% with respect to maltose, galactose, and xylose). The invention also provides a method for producing such an enzyme, and a composition for quantifying glucose using such an enzyme.

19 Claims, 2 Drawing Sheets

GLUCOSE DEHYDROGENASE

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 7,969 bytes ASCII (Text) file named "706577ReplacementSequenceListing.txt," created Sep. 21, 2010.

TECHNICAL FIELD

The present invention relates to a novel glucose dehydrogenase (GDH) that can be used as a reagent and a glucose sensor for measuring glucose concentration. The invention also relates to a method for producing such an enzyme, and to a composition for quantifying glucose containing such an enzyme, and a glucose sensor containing such an enzyme.

BACKGROUND ART

NAD(P)-dependent glucose dehydrogenase (EC 1.1.1.47; hereinafter, "glucose dehydrogenase" is sometimes referred to as "GDH", and "NAD(P)-dependent glucose dehydrogenase" as "NAD(P)-GDH") is an enzyme that is mainly used for blood glucose concentration measurement. This catalyst catalyzes the following reaction.

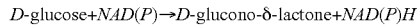

D-glucose+NAD(P)→D-glucono-δ-lactone+NAD(P)H

Glucose oxidase is also known as an enzyme that can be used for blood glucose measurement. However, this enzyme is said to have a problem in that glucose concentration measurement using glucose oxidase is affected by dissolved oxygen concentration because this enzyme may use molecular oxygen as an electron acceptor. Since glucose dehydrogenase is not influenced by such dissolved oxygen, this enzyme has been used as the main enzyme for blood glucose measurement in recent years. GDH enzymes include NAD(P)-dependent GDH, pyrroloquinoline quinone (PQQ)-dependent GDH, and flavin-dependent GDH. PQQ-dependent GDH, such as *Acinetobacter baumannii*-derived GDH, has a problem with substrate specificity in that PQQ-dependent GDH is as reactive with maltose as it is with glucose. Examples of known flavin-dependent GDH include *Aspergillus terreus*-derived GDH. Flavin-dependent GDH has stricter substrate specificity than PQQ-dependent GDH. However, flavin-dependent GDH does not necessarily have sufficient substrate specificity because its reactivity with xylose is about 9% relative to that with glucose. Furthermore, flavin-dependent GDH has a temperature stability of up to approximately 50° C., which is not sufficient.

Among known types of NAD(P)-GDH, *Bacillus* bacteria-derived NAD(P)-GDH is well known. For example, *Bacillus subtilis, Bacillus megaterium, Bacillus cereus*, etc., have been reported as strains that produce GDH. Although such bacteria-derived NAD(P)-GDH has a relatively high substrate specificity, its thermal stability is up to approximately 50° C. and is thus not sufficient.

Hyperthermophilic archaea are microorganisms that are systematically classified as Archeae, and that can grow at 90° C. or higher or have an optimum growth temperature of 80° C. or higher. The enzymes derived from hyperthermophilic archaea generally have high heat resistance. Many heat-resistant enzymes have been isolated from hyperthermophilic archaea and industrially utilized. NAD(P)-GDH has also been isolated from hyperthermophilic archaea, and the characteristics thereof have been investigated. *Sulforobus solfataricus*-derived GDH (Non-Patent Document 1), *Thermoplasma acidophilum*-derived GDH (Non-Patent Document 2), and *Thermoproteus tenax*-derived GDH (Non-Patent Document 3) have been reported in 1986, 1989, and 1997, respectively. Although these enzymes have excellent heat resistance, they have poor substrate specificity, compared to bacteria-derived enzymes. When NADP is used as a coenzyme, *Sulfolobus solfataricus*-derived GDH has a broader substrate specificity, and acts on galactose or xylose more strongly than on glucose at a substrate concentration of 40 mmol/L. When NAD is used as a coenzyme, specificity of *Sulfolobus solfataricus*-derived GDH for glucose is relatively increased, but its activity toward xylose is still high, i.e., about 26% relative to that toward glucose. When NADP is used as a coenzyme, the activity of *T. acidophilum*-derived GDH toward galactose is 70% relative to that toward glucose. *T. tenax*-derived GDH is also highly reactive with xylose. In blood glucose concentration measurement, the use of GDH that has low substrate specificity and high reactivity with substances other than glucose results in inaccurate blood glucose measurement, and is thus extremely disadvantageous. However, NAD(P)-GDH that is derived from hyperthermophilic archaea and that has a high heat resistance of 80° C. or higher and high specificity for glucose has not been known.

Non-Patent Document 1: Giardina P et al., Biochem. J., Vol. 239, pp. 517-522 (1986)
Non-Patent Document 2: Smith L D et al., Biochem. J., Vol. 261, pp. 793-797 (1989)
Non-Patent Document 3: Siebers B et al., Arch. Microbiol., Vol. 168, pp. 120-127 (1997)

DISCLOSURE OF THE INVENTION

Problems to be Solved by the Invention

Accordingly, it is an object of the invention to provide a glucose dehydrogenase that is an extremely stable enzyme having a thermostability of 80° C. or more, and that does not substantially act upon saccharides other than glucose; and to provide a method for producing such an enzyme and a composition for quantifying glucose containing such an enzyme.

Means for Solving The Problems

The inventors isolated hyperthermophilic archaea belonging to the genus *Thermoproteus* from hot-spring water obtained in Kodakara Island, Kagoshima Prefecture, Japan, and found that these archaea produce GDH. The inventors also found that the GDH has not only excellent thermostability, but also extremely high substrate specificity, unlike any other known GDHs derived from hyperthermophilic archaea. The inventors also succeeded in cloning a gene encoding the GDH, and expressing the gene that has been transferred to *Escherichia coli*. Furthermore, the inventors found that glucose concentration can be measured using this enzyme. The invention was accomplished based on these findings.

Specifically, the invention includes the following features.
Item 1: A glucose dehydrogenase having a reactivity of less than 3% with respect to maltose, galactose, and xylose, based on its reactivity with glucose, and having a temperature stability of 80° C. or more.
Item 2: The glucose dehydrogenase according to Item 1, utilizing nicotinamide adenine dinucleotide (NAD) or nicotinamide adenine dinucleotide phosphate (NADP) as a coenzyme in a glucose oxidation reaction.

Item 3. A glucose dehydrogenase derived from a hyperthermophilic archaeon, the glucose dehydrogenase having the following properties (A) to (F):
(A) temperature stability: 90° C. or less;
(B) pH stability: 4.8 to 9.7;
(C) optimum reaction temperature: 85° C.;
(D) optimum pH: 9.7;
(E) coenzyme: nicotinamide adenine dinucleotide (NAD) or nicotinamide adenine dinucleotide phosphate (NADP);
(F) substrate specificity: when NADP is utilized as the coenzyme, the glucose dehydrogenase exhibits an activity of 2% or more and less than 3% upon xylose and maltose, based on its activity upon glucose, and an activity of 1% or more and less than 2% upon galactose and mannose, based on its activity upon glucose, the glucose dehydrogenase being substantially unreactive with lactose, sorbitol, and sucrose; and
when NAD is used as the coenzyme, the glucose dehydrogenase is substantially unreactive with xylose, maltose, galactose, mannose, lactose, sorbitol, and sucrose.

Item 4: A glucose dehydrogenase having the amino acid sequence shown in SEQ ID NO. 2.

Item 5: A glucose dehydrogenase comprising an amino acid sequence resulting from deletion, substitution, insertion, or addition of one or more amino acids in the amino acid sequence shown in SEQ ID NO. 2, the glucose dehydrogenase having activity substantially equal to that of the glucose dehydrogenase having the amino acid sequence shown in SEQ ID NO. 2.

Item 6: DNA encoding the glucose dehydrogenase recited in any one of Items 1 to 5.

Item 7: An expression vector comprising the DNA recited in Item 6, the DNA being functionally coupled to a promoter operable in a host cell to which the DNA is introduced.

Item 8: A transformed microorganism transformed using the expression vector recited in Item 7.

Item 9: The transformed microorganism according to Item 8, wherein the microorganism is *Escherichia coli*.

Item 10: A method for producing the glucose dehydrogenase recited in any one of Items 1 to 5, comprising culturing the microorganism recited in Item 8 or 9, and collecting glucose dehydrogenase from the resulting culture.

Item 11. A composition for quantifying glucose, containing the glucose dehydrogenase recited in any one of Items 1 to 5.

Item 12: A method for quantifying glucose, comprising quantifying glucose using the glucose dehydrogenase recited in any one of Items 1 to 5.

Item 13: A glucose dehydrogenase comprising an amino acid sequence resulting from deletion, substitution, insertion, or addition of one or more amino acids in the amino acid sequence shown in SEQ ID NO. 2, the glucose dehydrogenase having activity substantially equal to that of a glucose dehydrogenase having the amino acid sequence shown in SEQ ID NO. 2.

Effects Of The Invention

The invention provides GDH that exhibits excellent stability, does not substantially act upon saccharides other than glucose, and is not affected by dissolved oxygen, thus enabling accurate measurement of blood glucose level and accurate quantification of glucose; and a glucose sensor containing the GDH and a composition for quantifying glucose containing the GDH.

BEST MODE FOR CARRYING OUT THE INVENTION

The invention relates to GDH that is derived from a hyperthermophilic archaeon and has high stability and excellent substrate specificity. The GDH specifically has the following properties. The GDH has substrate specificity such that it has a reactivity of less than 3% with respect to maltose, galactose, and xylose, based on its reactivity to glucose. The GDH has a temperature stability of 80° C. or more, preferably 85° C. or more, and more preferably 90° C. or more. More preferably, the GDH uses nicotinamide adenine dinucleotide (NAD) or nicotinamide adenine dinucleotide phosphate (NADP) as a coenzyme. More preferred properties of the GDH are detailed as follows: The temperature stability is 90° C.; the pH stability is 4.8 to 9.7; the optimum reaction temperature is 85° C.; the optimum pH is about 9.7; and the GDH functions using nicotinamide adenine dinucleotide (NAD) or nicotinamide adenine dinucleotide phosphate (NADP) as the coenzyme. The substrate specificity of the GDH is as follows: When NADP is utilized as the coenzyme, the glucose dehydrogenase exhibits an activity of 2% or more and less than 3% upon xylose and maltose, based on its activity upon glucose, and an activity of 1% or more and less than 2% upon galactose and mannose, based on its activity upon glucose, and the glucose dehydrogenase is substantially unreactive with lactose, sorbitol, and sucrose. When NAD is used as the coenzyme, the glucose dehydrogenase is substantially unreactive with xylose, maltose, galactose, mannose, lactose, sorbitol, and sucrose. The GDH has an estimated molecular weight of 37,000 based on its amino acid sequence.

According to the phylogenetic tree based on 16S ribosomal RNA (16SrRNA) (18SrRNA for eukaryotes) base sequences, organisms are broadly classified into the three domains of life, i.e., Eucarya, Bacteria, and Archaea. The term "archaeon" or "archaea" as used herein refers to organisms classified into the "Archaea" domain, based on the phylogenetic tree of 16SrRNA. Moreover, the term "hyperthermophilic archaeon" or "hyperthermophilic archaea" is defined as an archaeon or archaea that can be grown at 90° C. or more, or as an archaeon or archaea whose optimum growth temperature is 80° C. or more.

The organism from which the GDH of the invention is derived is not limited as long as it is a hyperthermophilic archaeon, but is preferably an archaeon that is classified as, or is a close relative of, a genus selected from the group consisting of the genus *Pyrodictium*, the genus *Sulfolobus*, the genus *Desulfurococcus*, the genus *Thermoproteus*, the genus *Thermofilum*, and the genus *Thermoplasma*, and more preferably is an archaeon classified as the genus *Thermoproteus*. Still more preferably, the organism from which the GDH of the invention is derived is an archaeon having the following features (A) to (G):

(A) The archaeon contains the base sequence shown in SEQ ID NO. 3 as the base sequence of the genomic DNA encoding the 16SrRNA.

(B) The archaeon can be grown at 80° C. or more; the optimum growth temperature is about 90° C.;

(C) The archaeon has a GC content of 58 to 62 mol % in the genomic DNA.

(D) The archaeon is a strictly anaerobic bacterium.

(E) The archaeon shows satisfactory growth when thiosulfate is added as an electron acceptor.

(F) The archaeon can be grown at a NaCl concentration of 1% or less.

(G) The archaeon is a long rod-shaped bacterium having a length of 10 to 30 μm and a width of about 5 μm.

The term "temperature stability" as used herein is defined as the residual ratio of GDH activity after heating relative to the GDH activity prior to heating when GDH is dissolved in 50 mM Tris-HCl, 0.1M NaCl (pH 8.0) at a concentration of 0.17 mg/ml, calculated as the protein concentration, and the GDH solution is heated for 30 minutes. The range of temperatures specified for temperature stability denotes the range of temperatures in which the GDH exhibits a residual activity ratio of 90% or more under the above-mentioned conditions. For example, the expression "thermostability of 80° C. or more" means that, after the GDH-containing solution is incubated for 30 minutes at 80° C. or more, the GDH retains at least 90% of its activity relative to that prior to heating. In other words, when the GDH is incubated for 30 minutes at a predetermined temperature, the range of temperatures at which the GDH, after incubation, has an activity of 90% or more relative to the activity prior to incubation includes temperatures of 80° C. or more. The method for measuring the GDH activity is as follows.

In a preferred embodiment, the term "thermostability" of the glucose dehydrogenase of the invention means that, after the glucose dehydrogenase is heat-treated for 30 minutes at a specific temperature, it has a residual activity of at least 90% relative to its enzymatic activity prior to heat treatment. For example, the expression "thermostability of 80° C." means that, after the GDH is heat-treated for 30 minutes at 80° C., the heat-treated GDH retains 90% or more of its enzymatic activity relative to that prior to heat treatment. Naturally, the "thermostability of 80° C." also means that the GDH retains a residual activity of 90% or more after it is heat-treated at a temperature below 80° C. (namely, the GDH has thermostability). As described above, the thermostability defined by a specific temperature means that, after the GDH of the invention is heat-treated at the specific temperature or less, the GDH has a residual activity of 90% or more. Therefore, the expression "thermostability of 80° C. or more" means that a temperature of 80° C. or more is the upper limit of thermostability.

In a further preferred embodiment, the term "thermostability" of the glucose dehydrogenase of the invention means that, after the glucose dehydrogenase is heat-treated for 30 minutes at a specific temperature, it has a residual activity of at least 95% relative to its enzymatic activity prior to heat treatment. For example, in this embodiment, the expression "thermostability of 80° C." means that, after the GDH is heat-treated for 30 minutes at 80° C., the heat-treated GDH retains 95% or more of its enzymatic activity relative to that prior to heat treatment. Naturally, the expression "thermostability of 80° C." also means that the GDH retains a residual activity of 95% or more after it is heat-treated at a temperature below 80° C. (namely, the GDH has thermostability).

The GDH of the invention has a thermostability of at least 80° C., preferably at least 85° C., and more preferably at least 90° C.

The term "substrate specificity" as referred to herein is evaluated as the rate at which the GDH oxidizes its substrate under the following conditions: a substrate concentration of 150 mmol/L, a coenzyme concentration of 5 mmol/L, a pH of 8.0, and a reaction temperature of 60° C. More specifically, according to the method for measuring the GDH activity described below, the activity of the GDH upon a saccharide other than glucose as the substrate to be evaluated is calculated, and the activity of the saccharide is expressed as a percentage, taking 100% as the activity of the GDH upon glucose as the substrate. In the invention, when the GDH activity upon a substrate is less than 1% based on the GDH activity upon glucose, the GDH is defined as "substantially unreactive" with the substrate.

The term "pH stability" as referred to herein is defined as the residual ratio of activity after incubation relative to the activity prior to incubation, when the GDH is dissolved in a solution containing 0.1 mol/L buffer at a concentration of 5 µg/mL calculated as the protein concentration, and the solution is incubated for 24 hours at 25° C. The range of temperatures specified for pH stability denotes the pH range in which the GDH exhibits a residual activity ratio of 90% or more under the above-mentioned conditions. For example, the expression "pH stability of 4.8 to 9.7" means that, after the GDH is incubated for 24 hours in a buffer of pH 4.8 to 9.7, the GDH retains at least 90% of its activity relative to that prior to incubation. In other words, the pH range at which the GDH after 24 hours of incubation at a predetermined pH has an activity of 90% or more relative to that prior to incubation includes pH values of 4.8 to 9.7.

The GDH of the invention is not limited as long as it is derived from a hyperthermophilic archaeon and has the above-mentioned properties. The expression "derived from a hyperthermophilic archaeon" means that a strain found in the nature that inherently produces the GDH is a hyperthermophilic archaeon. Therefore, any GDH produced from artificially engineered cells by, for example, genetic transformation, is herein defined as being derived from a hyperthermophilic archaeon, if the GDH meets the following conditions: the base sequence of the gene is identical to that of the gene inherently present in the genome of a hyperthermophilic archaeon; or the base sequence of the gene is a sequence resulting from substitution, deletion, insertion, or addition of one or more bases of the gene inherently present in the genome of a hyperthermophilic archaeon, and the gene has activity substantially equal to that of the GDH of the invention. The expression "activity substantially equal" means that the activity of the modified GDH is within experimental error, or equal to or more than the activity of the GDH having the amino acid sequence shown in SEQ ID NO. 2.

A preferred embodiment of the invention provides a glucose dehydrogenase containing a polypeptide consisting of the amino acid sequence shown in SEQ ID NO. 2, or a glucose dehydrogenase containing a polypeptide consisting of an amino acid sequence resulting from deletion, substitution, insertion, or addition of one or more amino acid residues in the amino acid sequence shown in SEQ ID NO. 2. The GDH may be produced from a culture obtained by culturing a hyperthermophilic archaeon from which the GDH is derived. The GDH may also be produced by expressing a gene that has been transferred to a host organism different from the hyperthermophilic archaeon from which the GDH is derived.

When the glucose dehydrogenase of the invention is a polypeptide having one or more amino acid substitutions, additions, deletions, or insertions in the amino acid sequence shown in SEQ ID NO. 2, the number and types of such amino acid mutations are not limited as long as they do not affect glucose dehydrogenase activity, and enzyme properties such as the thermostability, pH stability, and substrate specificity mentioned above. The number of mutations is preferably plural, more specifically 1 to 30, preferably 1 to 15, more preferably 1 to 10, still more preferably 1 to 5, and even more preferably 1 to 3.

When the glucose dehydrogenase of the invention is a polypeptide having one or more amino acid substitutions in the amino acid sequence shown in SEQ ID NO. 2, the amino acid substitutions are not limited as long as they do not impair the glucose dehydrogenase activity and the above-mentioned enzyme properties. Preferably, however, the amino acid substitutions are substitutions by similar amino acids. Examples of similar amino acids include the following:
aromatic amino acids: Phe, Trp, Tyr
aliphatic amino acids: Ala, Leu, Ile, Val
polar amino acids: Gln, Asn
basic amino acids: Lys, Arg, His
acidic amino acids: Glu, Asp
amino acids with hydroxy groups: Ser, Thr The polypeptide sequence shown in SEQ ID NO. 2 has high homology, i.e., 79%, to the sequence of known GDH derived from *Thermoproteus tenax*. However, the GDH of the invention clearly differs from the known GDH in terms of its extremely high substrate specificity. According to Non-Patent Document 3 listed above, the known GDH derived from *Thermoproteus tenax* has an activity upon xylose higher than that upon glucose at a substrate concentration of 40 mmol/L. By contrast, the GDH of the invention, when using NADP as the coenzyme, has an activity upon xylose of less than 3% based on its activity upon glucose, even at a high substrate concentration, i.e., 150 mmol/L. When using NAD as the coenzyme, the GDH of the invention has an activity upon xylose of less than 1% based on its activity upon glucose. Thus, the GDH is marked by its extremely low reactivity with xylose. This difference in properties between the GDH of the invention and the known GDH can be largely attributed to differences in their amino acid sequences. One of the characteristics of the GDH of the invention is that it has an amino acid sequence having high homology to the sequence of SEQ ID NO. 2. Specifically, the GDH has 80% or more homology, preferably 85% or more homology, and more preferably 90% or more homology to the amino acid sequence of SEQ ID NO. 2. In a further preferred embodiment, the GDH of the invention has 95% or more homology, more preferably 98% or more homology, and still more preferably 99% or more homology to the amino acid sequence shown in SEQ ID NO. 2.

The GDH of the invention can be obtained by suitably using, for example, any of the following methods:

(1) extracting the GDH from a source, which is a cell that produces the enzyme, followed by purification;

(2) chemically synthesizing the GDH;

(3) purifying the GDH from cells engineered to express the GDH by gene recombination technology; and (4) biochemically synthesizing the GDH from a nucleic acid encoding the GDH, using a cell-free transcription/translation system.

One example of a method for producing natural cells that produce the GDH of the invention is, for example, as follows. First, a sample is collected from a favorable growth environment for hyperthermophilic archaea, i.e., high-temperature environments such as volcanic regions, the deep subsurface, submarine hydrothermal vents, and regions where hot-springs occur, and the sample is inoculated into a suitable medium and cultured at 80° C. or more.

The isolation/purification of GDH from natural GDH-producing cells can be performed, for example, as follows. The GDH-producing cells are homogenized in a suitable buffer, and a cell extraction solution is obtained by sonication, surfactant treatment, or the like. The purification of GDH can then be performed by suitably combining separation techniques routinely used in the separation and purification of proteins. Non-limiting examples of such separation techniques include methods utilizing the difference in solubility, such as salting out and solvent precipitation; methods utilizing the difference in molecular weight, such as dialysis, ultrafiltration, gel filtration, unmodified polyacrylamide electrophoresis (PAGE), and sodium dodecyl sulfate-polyacrylamide electrophoresis (SDS-PAGE); methods utilizing charges, such as ion exchange chromatography and hydroxyapatite chromatography; methods utilizing specific affinity, such as affinity chromatography; methods utilizing the difference in hydrophobicity, such as reversed phase high performance liquid chromatography; and methods utilizing the difference in isoelectric points, such as isoelectric focusing.

The production of GDH by chemical synthesis can be performed by synthesizing all or a portion of its sequence based on, for example, the amino acid sequence shown in SEQ ID NO. 2, by using a peptide synthesizer. The peptide synthesis method may, for example, be solid-phase synthesis or liquid-phase synthesis. The protein of interest can be produced by condensation of a partial peptide or amino acids that can form the GDH of the invention and remaining portions. Where the product contains a protective group, the protective group is removed. The condensation and removal of a protective group are performed according to known methods, for example, the methods described in the following documents (1) and (2):

(1) M. Bodanszky and M. A. Ondetti, *Peptide Synthesis*, Interscience Publishers, New York (1966)

(2) Schroeder and Luebke, *The Peptide*, Academic Press, New York (1965).

The thus-obtained GDH of the invention can be purified/isolated according to a known purification method. Examples of purification methods include solvent extraction, distillation, column chromatography, liquid chromatography, recrystallization, and combinations thereof.

When the GDH obtained by the above-mentioned methods is a free entity, it can be converted to a suitable salt according to a known method or a method utilizing known methods. Conversely, when the GDH is obtained as a salt, the salt can be converted to a free entity or another salt according to a known method or a method utilizing known methods.

Preferably, the GDH of the invention can be produced by cloning (or chemically synthesizing) a nucleic acid encoding the GDH protein, and by isolating/purifying GDH from a culture of a transformant containing an expression vector bearing the nucleic acid.

Cloning enzyme genes can typically be performed according to the following method. A desired enzyme is completely or partially purified from cells or tissue that produces the enzyme, and an amino acid sequence at the N terminus is determined by Edman analysis and mass spectrometry. The amino acid sequence of an oligopeptide obtained by partially digesting the enzyme using a protease or chemical substance that cleaves the peptide in a sequence-specific manner is likewise determined by Edman analysis and mass spectrometry. An oligonucleotide having a base sequence corresponding to the thus-determined partial amino acid sequence is synthesized, and, using the oligopeptide as a probe, the DNA encoding the enzyme is cloned by colony (or plaque) hybridization from a cDNA or genomic DNA library prepared from cells or tissue that produces the enzyme. Alternatively, using all or a portion of a completely or partially purified enzyme as an antigen, an antibody against the enzyme is prepared according to a routine method, and DNA encoding the enzyme is cloned by antibody screening from a cDNA or genomic DNA library prepared from cells or tissue that produces the enzyme.

Where the gene of an enzyme having enzymatic properties similar to those of the enzyme of interest is known, it is possible to access, for example, the homepage of NCBI BLAST (www.ncbi.nlm.nih.gov/BLAST/), search for a sequence having homology to the base sequence of the known gene, prepare a probe as described above based on the base sequence that has been found, and clone DNA encoding the enzyme of interest by colony (or plaque) hybridization.

Alternatively, it is possible to synthesize appropriate oligonucleotides as primers based on the base sequence that has been found, and perform direct amplification using Polymerase Chain Reaction (hereinafter abbreviated to "PCR") or Reverse Transcriptase-PCR (hereinafter "RT-PCR"), using, as a template, a genomic DNA fraction, total RNA, or an mRNA fraction prepared from GDH-producing cells.

The base sequence of the thus-obtained DNA can be determined using a known sequencing technique such as the Maxam-Gilbert method or dideoxy chain-termination method.

More preferably, the nucleic acid encoding the GDH of the invention is, for example, a nucleic acid containing the base sequence shown in SEQ ID NO. 1 (when the nucleic acid is RNA, "t" is replaced with "u"); or a nucleic acid containing a base sequence hybridized under stringent conditions to a base sequence complementary to the base sequence shown in SEQ ID NO. 1, the nucleic acid encoding a polypeptide having properties identical to those of the above-described polypeptide consisting of the amino acid sequence shown in SEQ ID NO. 2. Specifically, the polypeptide has a molecular weight of 37,000 as estimated by SDS-PAGE, a temperature stability of 90° C. or less, a pH stability of 4.8 to 9.7, an optimum reaction temperature of 85° C., an optimum pH of about 9.7, and a substrate specificity such that it does not substantially act upon maltose, galactose, xylose, lactose, sorbitol, and mannose. The polypeptide functions using, as a coenzyme, nicotinamide adenine dinucleotide (NAD) or nicotinamide adenine dinucleotide phosphate (NADP). Examples of nucleic acids hybridized under stringent conditions to the base sequence shown in SEQ ID NO. 1 include nucleic acids containing base sequences having 60% or more homology, preferably 70% or more homology, more preferably 80% or more homology, still more preferably 90% or more homology, and most preferably 95% or more homology to the base sequence shown in SEQ ID NO. 1.

The homology of base sequences can be herein calculated using the homology calculation algorithm, NCBI BLAST (National Center for Biotechnology Information Basic Local Alignment Search Tool), under the following conditions (expected value=10; gap allowed; filtering=ON; match score=1; mismatch score=−3). The above-mentioned homology calculation algorithm for amino acid sequences can also be mentioned as another preferable example of an algorithm for determining the homology of base sequences.

Hybridization can be performed according to a known method or a method utilizing known methods, for example, the method described in *Molecular Cloning,* 2nd Edition (J. Sambrook et al., Cold Spring Harbor Lab. Press, 1989). When a commercially available library is used, hybridization can be performed according to the method described in the attached manual. Hybridization can be preferably performed according to stringent conditions.

Examples of stringent conditions are as follows: sodium salt concentration: about 19 to about 40 mM, and preferably about 19 to about 20 mM; temperature: about 50° C. to about 70° C., and preferably 60° C. to about 65° C. Specifically, a sodium salt concentration of about 19 mM and a temperature of about 65° C. are preferred. Those skilled in the art can readily adjust the hybridization conditions to the desired stringency, by varying the salt concentration of the hybridization solution, the temperature of the hybridization reaction, the probe concentration, the probe length, the number of mismatches, the hybridization reaction time, the salt concentration of the washing solution, the washing temperature, and the like.

The DNA encoding the GDH of the invention can be obtained from the genomic DNA or RNA (cDNA) of a hyperthermophilic archaeon of the genus *Thermoproteus*, as described above. Alternatively, the DNA encoding the GDH can be obtained by chemically synthesizing the DNA chain, or by synthesizing partially overlapping short oligo DNA, and connecting the oligo DNA using PCR, thereby constructing DNA encoding the full length of the GDH gene. The advantage of chemical synthesis or constructing the full-length DNA using PCR in combination, is that the codons used can be designed across the full length of the gene according to the host to which the gene is introduced. Codons encoding the same amino acid are not uniformly used; codon usage varies depending on the species of organism. In general, a gene that is highly expressed in a particular species of organism contains codons frequently used in the organism. Conversely, it is often the case that the presence of infrequently used codons prevents a gene with a low level of expression from being highly expressed. Concerning the expression of foreign genes, there have been many reports of cases where the level of expression of a foreign protein is increased by replacing the codons in the gene sequence with codons that are frequently used in the host organism. Thus, such modification of the codons used is expected to enhance the level of expression of a foreign gene.

It is, therefore, desired to modify the codons of the DNA encoding the GDH of the invention into codons more suitable for the host to which the DNA is introduced (i.e., codons frequently used in the host). The codon usage in each host is defined as the ratio of each codon used in all of the genes present in the genome sequence of the host organism, and is represented by, for example, the number of times that each codon is used per 1,000 codons. For an organism whose entire genome sequence is yet unknown, codon usage can be approximately calculated from the sequences of representative genes of the organism. The data on codon usage in the host organism for recombination are available, for example, in the Codon Usage Database published on the homepage of the Kazusa DNA Research Institute. Alternatively, the user may refer to documents disclosing codon usage in various organisms, or may determine by him/herself the codon usage data for the host organism to be used. Referring to the codon usage data obtained, as well as the gene sequence to be introduced to the host, codons infrequently used in the host organism may be replaced with frequently used codons encoding the same amino acid.

The host cell to which the DNA encoding the GDH of the invention is introduced is not limited as long as recombinant expression systems therefor have been established, as described below. Examples of preferable host cells include microorganisms such as *Escherichia coli, Bacillus subtilis*, and other bacteria, *Actinomycetes, Aspergillus*, and yeast, as well as insect cells, animal cells and higher plant cells. *Escherichia coli* (for example, K12 strain and B strain) is preferred. Examples of frequently used codons in *Escherichia coli* include, taking the K12 strain as an example, the following: GGT or GGC for Gly; GAA for Glu; GAT for Asp; GTG for Val; GCG for Ala; CGT or CGC for Arg; AGC for Ser; AAA for Lys; ATT or ATC for Ile; ACC for Thr; CTG for Leu; CAG for Gln; and CCG for Pro.

The DNA encoding the GDH wherein the codons have been replaced with codons that are frequently used in the host may, for example, be DNA obtained by replacing the codons of the DNA encoding the GDH derived from an archaeon of the genus *Thermoproteus* with codons that are frequently used in the *Escherichia coli* K12 strain and encode the same amino acid sequence as that of the GDH.

The invention also provides a recombinant vector containing the DNA encoding the GDH of the invention. The recombinant vector of the invention is not limited as long as it can keep its replication or autonomically replicate in various host cells of prokaryotic and/or eucaryotic cells. The recombinant vector includes plasmid vectors and viral vectors. The recombinant vector can be readily prepared by linking the DNA encoding the GDH of the invention to a known cloning vector or expression vector available in the art, using a suitable restriction enzyme and ligase, or, if necessary, additionally using a linker or adaptor DNA. Alternatively, if the DNA encoding the GDH is a gene fragment amplified using a DNA polymerase such as Taq polymerase that adds one base to an amplified end, the DNA can be connected to the vector by TA cloning.

Examples of plasmid vectors include *Escherichia coli*-derived plasmids such as pBR322, pBR325, pUC18, and pUC19; yeast-derived plasmids such as pSH19 and pSH15; and *Bacillus subtilis*-derived plasmids such as pUB110, pTP5, and pC194. Examples of viral vectors include bacteriophages such as λ phage; papovaviruses such as SV40 and bovine papillomavirus (BPV); retroviruses such as Moloney murine leukemia virus (MoMuLV); and animal and insect viruses such as adenovirus (AdV), adeno-associated virus (AAV), vaccinia virus, and baculovirus.

More particularly, the invention provides a GDH expression vector that contains DNA encoding GDH under the control of a functional promoter within a target cell.

The vector used herein is not limited as long as it contains:

a promoter region capable of functioning within various prokaryotic and/or eukaryotic host cells to control the transcription of the gene located downstream of the promoter region (e.g., in the case of *Escherichia coli* host cells, trp promoter, lac promoter, lecA promoter, etc.; in the case of *Bacillus subtilis* host cells, SPO1 promoter, SPO2 promoter, penP promoter, etc.; in the case of yeast host cells, PHO5 promoter, PGK promoter, GAP promoter, ADH promoter, etc.; in the case of mammalian host cells, viral promoters such as SV40-derived initial promoter, MoMuLV-derived long terminal repeat, adenovirus-derived initial promoter, etc.); and a transcription termination signal for the gene, i.e., a terminator region; wherein:

the promoter region and terminator region are linked via at least one restriction enzyme recognition site, which is preferably a sequence containing a unique restriction site that cuts the vector at the position of the site only.

Preferably, the vector further contains a selective marker gene for selecting transformants (the selective marker gene including genes that impart drug resistance, such as tetracycline, ampicillin, kanamycin, hygromycin, and phosphinothricin; and genes that compensate via auxotrophic mutation). Moreover, when the DNA to be inserted that encodes GDH does not contain the initiation codon and termination codon, it is preferred to use a vector containing the initiation codon (ATG or GTG) and termination codon (TAG, TGA, TAA) downstream of the promoter region and upstream of the terminator region, respectively.

When bacteria are used as host cells, it is typically necessary that the expression vector contain, in addition to the promoter region and terminator region, a replicon capable of autonomous replication within the host cell. The promoter region contains an operator and a Shine-Dalgarno (SD) sequence in the vicinity of the promoter.

When yeast, an animal cell, or an insect cell is used as the host, the expression vector preferably further contains an enhancer sequence, 5' and 3' untranslated regions of the GDH mRNA, a polyadenylation site, and the like.

Examples of host organisms to which the prepared recombinant vector is introduced include host organisms for which recombinant expression systems have been established, for example, microorganisms such as *Escherichia coli, Bacillus subtilis*, and other bacteria, *Actinomycetes, Aspergillus*, and yeast, as well as insect cells, animal cells and higher plant cells. Among these, *Escherichia coli* is preferably used because of its excellent protein expression ability. The recombinant plasmid can be introduced by, for example, electroporation. In the case of cells made competent by chemical treatment using calcium chloride or the like, the recombinant plasmid can be introduced by applying heat shock. Host microorganisms to which the target recombinant plasmid is transferred may be selected by searching for a microorganism that expresses both the GDH activity and a marker gene of the vector containing the target DNA, such as any of various drug-resistant genes. For example, a microorganism that grows on a selective medium suitable for the drug-resistant gene, and also expresses GDH, may be selected.

The GDH of the invention can be produced by culturing a transformant containing the thus-prepared GDH expression vector in a medium, and collecting GDH from the resulting culture.

Preferably, the medium contains a carbon source or an inorganic or organic nitrogen source necessary for the growth of the host cell (transformant). Examples of carbon sources include glucose, dextran, soluble starch, and sucrose; and examples of inorganic or organic nitrogen sources include ammonium salts, nitrates, amino acids, corn steep liquor, peptones, casein, meat extracts, defatted soybeans, and potato extracts. The medium may optionally contain other nutrients, for example, inorganic salts (e.g., calcium chloride, sodium dihydrogenphosphate, and magnesium chloride), vitamins, and antibiotics (e.g., tetracycline, neomycin, ampicillin, and kanamycin).

Culturing is performed according to a method known in the art. Specific media and culture conditions used according to the host cell are given below as examples, but the culture conditions used in the invention are by no means limited thereto.

When bacteria, Actinomycetes, yeast, filamentous fungi, and the like are used as hosts, examples of suitable media are liquid media containing the above-mentioned nitrogen source. Preferably, the media have a pH of 5 to 9. When the host is *Escherichia coli*, examples of preferable media are LB medium and M9 medium [Miller. J., *Exp. Mol. Genet, p.* 431, Cold Spring Harbor Laboratory, and New York (1972)]. Culturing can be typically performed for about 3 to about 72 hours at 14 to 43° C., under aeration and agitation, as required. When the host is *Bacillus subtilis*, culturing can typically be performed for about 16 to about 96 hours at 30 to 40° C., under aeration and agitation, as required. When the host is yeast, an example of a medium is Burkholder minimal medium [Bostian. K L. et al., *Proc. Natl. Acad. Sci.* USA, 77, 4505 (1980)], with a pH of preferably 5 to 8. Culturing can be typically performed for about 14 to about 144 hours at about 20 to about 35° C., under aeration and agitation, as required.

When the host is an animal cell, examples of media are a minimal essential medium (MEM) containing about 5-20% fetal bovine serum [*Science,* 122, 501 (1952)], Dulbecco's Modified Eagle's Medium (DMEM) [*Virology,* 8, 396 (1959)], RPMI1640 medium [*J. Am. Med. Assoc.,* 199, 519 (1967)], and 199 medium [*Proc. Soc. Exp. Biol. Med.,* 73, 1 (1950)]. The pH of the media is preferably about 6 to about 8. Culturing can be typically performed for about 15 to about 72 hours at about 30 to about 40° C., under aeration and agitation, as required.

When the host is an insect cell, an example of a medium is Grace's medium containing fetal bovine serum [*Proc. Natl. Acad. Sci.* USA, 82, 8404 (1985)], with a pH of preferably about 5 to about 8. Culturing can be typically performed for 15 to 100 hours at about 20 to about 40° C., under aeration and agitation, as required.

Purification of GDH can be performed by suitably combining various generally used separation techniques, according to the fraction in which the GDH activity is present.

The GDH present in the medium of the culture can be isolated/purified by obtaining the culture supernatant (filtrate) by centrifugation or filtering of the culture, and separating the GDH from the culture supernatant using a known separation method suitably selected from, for example, salting out, solvent precipitation, dialysis, ultrafiltration, gel filtration, unmodified PAGE, SDS-PAGE, ion exchange chromatography, hydroxylapatite chromatography, affinity chromatography, reversed phase high performance liquid chromatography, and isoelectric focusing.

The GDH present in the cytoplasm can be isolated/purified by collecting cells by centrifugation or filtering of the culture, suspending the cells in a suitable buffer, disrupting (lysing) the cells and organelles by, for example, sonication, lysozyme treatment, freezing/thawing, osmotic shock, and/or surfactant treatment using Triton-X100 or the like, followed by removal of debris by centrifugation, filtration, or the like, to yield a soluble fraction, and processing the soluble fraction according to the method as described above.

An example of a preferable means for rapidly and easily obtaining recombinant GDH is a method wherein a DNA sequence encoding an amino acid sequence that can adsorb to a metal ion chelate (e.g., a sequence consisting of basic amino acids such as histidine, arginine, or ricin, with histidine being preferred) is added by genetic engineering to a portion containing the coding sequence of the GDH (preferably at the N or C terminus), and the resulting material is expressed in a host cell; subsequently, the GDH is separated/collected from the fraction having the GDH activity of the cell culture, based on the affinity of the amino acid sequence for the immobilized support of the metal ion chelate. The DNA sequence encoding an amino acid sequence that can adsorb to a metal ion chelate can be introduced to the coding sequence of the GDH, for example, as follows: in the process of cloning DNA encoding the GDH, performing PCR amplification using a hybrid primer in which the DNA sequence is linked to the base sequence encoding the C-terminal amino acid sequence of the GDH; or by inserting the DNA encoding the GDH in-frame to an expression vector containing the DNA sequence prior to the termination codon.

The metal ion chelate adsorbent used for purification is prepared by bringing a transition metal, for example, a divalent ion such as cobalt, copper, nickel, or iron, or a trivalent ion such as iron or aluminum, and preferably a divalent ion-containing solution of cobalt or nickel, into contact with a matrix to which a ligand, for example, an iminodiacetic acid (IDA) group, nitrilotriacetic acid (NTA) group, or tris(carboxymethyl)ethylenediamine (TED) group, is attached, thereby binding the transition metal to the ligand. The matrix portion of the chelate adsorbent is not limited as long as it is a general insoluble support.

Alternatively, affinity purification can be performed using glutathione-S-transferase (GST), maltose binding protein (MBP), HA, a FLAG peptide, or the like as a tag.

The above-described purification step may optionally include treatments such as membrane concentration, concentration under reduced pressure, and the addition of an activator and/or a stabilizer. Since the GDH of the invention has excellent heat resistance, heat treatment that heat-denatures contaminating proteins derived from other host cells, and that allows the GDH activity to be retained is especially effective for substantially enhancing the GDH purity. Although the solvents used in these steps are not limited, preferable solvents are various buffers having buffer capacity at a pH ranging from about 6 to about 9, such as K-phosphate buffer, tris-hydrochloric acid buffer, and Good's buffers.

When the thus-obtained GDH is a free entity, it can be converted to a salt according to a known method or a method utilizing known methods. When the GDH is obtained as a salt, the salt can be converted to a free entity or another salt according to a known method or a method utilizing known methods.

The purified enzyme can be industrially utilized in a liquid form, or can be powdered or granulated. Powderization of liquid enzyme may be performed by freeze-drying according to a routine method.

Furthermore, the GDH of the invention can be synthesized by in vitro translation using the RNA complementary to the DNA encoding the GDH as a template, and using a cell-free protein translation system including rabbit reticulocyte lysate, wheat germ lysate, *Escherichia coli* lysate, and the like.

RNA encoding the GDH of the invention can be obtained by purifying the mRNA encoding the GDH of the invention according to a routine method. Alternatively, RNA encoding the GDH of the invention can be obtained by preparing cRNA using DNA encoding the GDH as a template, and using a cell-free transcription system including RNA polymerase. A commercially available cell-free protein transcription/translation system can be used, or a cell-free protein transcription/translation system can be prepared according to a known method; specifically, *Escherichia coli* extract can be prepared according to, for example, the method described in Pratt J. M. et al., "Transcription and Translation", Hames B. D. and Higgins S. J. eds., IRL Press, Oxford 179-209 (1984). Examples of commercially available cell lysates are as follows: cell lysates derived from *Escherichia coli* include *E. coli* S30 Extract System (manufactured by Promega), and RTS 500 Rapid Translation System (manufactured by Roche); cell lysates derived from rabbit reticulocytes include Rabbit Reticulocyte Lysate System (manufactured by Promega); and cell lysates derived from wheat germ include PROTEIOS™ (manufactured by TOYOBO). Preferred among the above is wheat germ lysate.

Examples of usable methods for preparing wheat germ lysate are the method described in Johnston F. B. et al., *Nature*, 179: 160-161 (1957), and the method described in Erickson A. H. et al., *Meth. Enzymol.*, 96: 38-50 (1996).

Examples of systems or apparatuses for protein synthesis include a batch method [Pratt, the J. M. et al. (1984), supra]; a continuous system for the synthesis of cell-free proteins wherein amino acids, energy sources, and the like are continuously fed to the reaction system [Spirin A. S. et al., *Science*, 242: 1162-1164 (1988)]; dialysis (Kigawa et al., the 21st Annual Meeting of the Molecular Biology Society of Japan, WID6); and a bilayer method (instructions for use of PROTEIOS™ wheat germ cell-free protein synthesis core kit; manufactured by TOYOBO). Further examples of usable methods include a method wherein a template RNA, amino acids, energy sources, and the like are supplied to the synthesis reaction system as required, and the synthesized or degradation products are discharged from the reaction system as required (Japanese Unexamined Patent Publication No. 2000-333673).

The invention also provides a composition for quantifying glucose containing the GDH of the invention and a method for measuring the glucose concentration using the GDH of the invention.

In the invention, the glucose level can be measured by various methods as follows. The reagent for measuring the glucose level of the invention, the glucose assay kit, and the glucose sensor of the invention may take various forms, such as liquid forms (a solution, suspension, etc.), powdery forms obtained by, for example, vacuum drying or spray drying, and freeze-dried forms. The freeze-drying method is not limited, and may be performed according to a routine method. Instead of being a freeze-dried product, the composition containing the enzyme of the invention may also be in the form of a solution obtained by reconstituting the freeze-dried product.

Reagent for Measuring the Glucose Level

The reagent for measuring the glucose level of the invention typically includes the GDH of the invention, a coenzyme, a buffer, glucose standard solutions for preparing a calibration curve, and instructions for use. Preferably, the reagent includes reagents necessary for the assay such as a mediator.

Glucose Assay Kit

The glucose assay kit of the invention typically includes reagents necessary for the assay such as the GDH of the invention, a coenzyme, a buffer, a mediator, and the like, glucose standard solutions for preparing a calibration curve, and instructions for use. The kit of the invention can be provided as, for example, a freeze-dried reagent or a solution in a suitable storage solution.

Glucose Sensor

The glucose sensor of the invention uses a carbon electrode, a gold electrode, a platinum electrode, or the like as an electrode, on which the GDH is immobilized. Examples of methods for immobilization include a method using a crosslinking reagent, a method of enfolding the GDH in a polymer matrix, a method of covering the GDH with a dialysis membrane, and methods using a photo-crosslinkable polymer, a conductive polymer, a redox polymer, or the like. Alternatively, the GDH may be immobilized in a polymer or adsorbed/immobilized onto the electrode, together with a coenzyme such as NAD or NADP, or an electron mediator such as ferrocene or its derivative. These methods may also be used in combination. The GDH of the invention may be immobilized onto the electrode together with NAD or NADP as a coenzyme. Alternatively, the GDH may be immobilized onto the electrode in the absence of a coenzyme, and a coenzyme may be supplied as another layer, or in a solution. Typically, the GDH of the invention is immobilized on a carbon electrode using glutaraldehyde, and the glutaraldehyde is subsequently blocked by a treatment using a reagent having an amine group.

The glucose concentration can be measured as follows. A reaction solution containing a buffer, GDH, and NAD or NADP as a coenzyme is placed in a cell at constant temperature, and the temperature is kept constant. A sample containing glucose is added thereto and reacted for a given number of hours at a given temperature. During this time, the absorbance at 340 nm is monitored. The glucose concentration in the sample can be calculated based on the calibration curve previously prepared using glucose solutions with a standard concentration. In the case of rate measurement, the glucose concentration is calculated from the rate of increase in absorbance per unit time. In the case of endpoint measurement, the glucose concentration is calculated from the increase in absorbance measured until all the glucose in the sample is oxidized. Moreover, when glucose is quantified using a calorimetric method in the visible light region, a suitable mediator and a coloring agent may further be added. For example, glucose can be quantified by adding 2,6-dichlorophenolindophenol (DCPIP) or the like, and monitoring a decrease in absorbance at 600 nm. Alternatively, the glucose concentration can be determined by adding phenazine methosulfate (PMS) as a mediator, and nitrotetrazolium blue (NTB) as a coloring reagent, and by measuring the absorbance at 570 nm, thereby determining the amount of diformazan produced. The mediator and color reagent used are by no means limited to those mentioned above.

The glucose concentration can also be measured as follows. The buffer is placed in a cell at constant temperature; a coenzyme and, as required, a mediator, are added; and the temperature is kept constant. Potassium ferricyanide, phenazine methosulfate, or the like can be used as a mediator. As a working electrode, the electrode on which the GDH of the invention has been immobilized is used, and a counter electrode (e.g., platinum electrode) and a reference electrode (e.g., Ag/AgCl electrode) are used. A certain voltage is applied to the carbon electrode; after the current has become constant, a sample containing glucose is added, and an increase in current is measured. The glucose concentration in the sample can be calculated according to the calibration curve prepared from glucose solutions with a standard concentration.

Example of GDH Activity Measurement

In the invention, the GDH activity is measured according to the following method, unless otherwise stated.

900 µL of a reaction solution (90 mmol/L Bicine, 5 mmol/L β-NADP+, 150 mmol/L D-glucose) is transferred to a quartz cell with a lid, and pre-heated for 5 minutes at 60° C. 15 µL of a GDH solution is mixed with the reaction solution, and reacted for 3 minutes at 60° C.; during the reaction, absorbance at 340 nm is measured. An increase in absorbance per minute ($\Delta OD_{TEST}$) is calculated from a linear portion of the change in absorbance. As a blank test, the buffer is mixed with the reaction solution instead of the GDH solution, and incubated for 3 minutes at 60° C. as described above; absorbance at 340 nm is recorded, and the change in absorbance per minute ($\Delta OD_{BLANK}$) is calculated. The thus-obtained values are substituted into the following equation, and the activity value (U/mL) is calculated. Here, one unit (U) is defined as the amount of enzyme that reduces 1 micromole of coenzyme per minute in the presence of a substrate.

$$\text{Activity(U/mL)} = [(\Delta OD_{TEST} - \Delta OD_{BLANK}) \times 0.915 \times \text{dilution factor}]/(6.22 \times 1.0 \times 0.015)$$

wherein:

915: volume (mL) of the mixture after adding the GDH solution;

6.22: millimoler molecular extinction coefficient ($cm^2$/micromole) of NADPH;

0: optical path length (cm); and

015: the liquid volume (mL) of the GDH solution added.

Quantification of Protein

The amount of protein as referred to herein is measured by the Bradford method. More specifically, a protein concentration measurement kit, Bio-Rad Protein Assay, manufactured by Bio-Rad, is used, and measurement is conducted according to the manual attached to the kit. The protein concentration is determined using a calibration curve prepared using bovine serum albumin (BSA). Thus, the amount of protein as referred to herein is calculated in terms of BSA equivalents.

EXAMPLES

The present invention is specifically described below with reference to the following examples; however, the present invention is not limited to these examples.

Example 1

Cultivation of Hyperthermophilic Archaea and Purification of GDH

The inventors isolated hyperthermophilic archaea from hot spring water in Kotakara Island in Kagoshima Prefecture. From its base sequence of 16SrRNA, this strain was assumed to be a strain of bacteria classified in the genus *Thermoproteus*, having the following features (A) to (G): (A) The bacteria contain the base sequence shown in SEQ ID NO. 3 as the base sequence of the genomic DNA encoding the 16SrRNA; (B) the bacteria can be grown at 80° C. or more; the optimum growth temperature is about 90° C.; (C) the bacteria have a GC content of 58 to 62 mol % in the genomic DNA; (D) the bacteria are strictly anaerobic; (E) the bacteria show satisfactory growth when thiosulfate is added as an electron acceptor; (F) the bacteria can be grown at a NaCl concentration of 1% or less; and (G) the bacteria are long rod-shaped, with a length of 10 to 30 μm and a width of about 5 μm. This strain having the above-described characteristics is named *Thermoproteus* sp. GDH-1 strain (*Thermoproteus* sp. GDH1).

In order to cultivate GDH1, a medium containing the following components was placed in an anaerobic glove box: 0.5% tryptone, 0.5% yeast extract, 0.5% sodium thiosulfate, 0.5% sodium chloride, 0.005% sodium sulfide, and resazurin (5 mg/L) as an indicator of dissolved oxygen. Then, oxygen was removed from the medium by repeatedly performing nitrogen replacement. The above-described isolated strain was inoculated in this medium, and stationary cultured at 85° C. for 3 days. Further, grown microbial cells were subcultured into a medium in which glucose with a final concentration of 0.5% was added to the above-described medium composition, and these cells were anaerobically cultured at 85° C. for 3 days. The culture (7 L) was centrifuged using a high speed cooling centrifugal machine, and the supernatant was removed, thereby collecting microbial cells. These microbial cells were suspended in 20 mL of 50 mM potassium phosphate buffer (pH 7.0). This suspension was placed on ice, and treated for 10 minutes using an ultrasonic crusher (TOMY SEIKO CO., LTD, UD-201) at a output level of 3 and at a duty cycle of 40%, thereby crushing the microbial cells. The crushed cell solution was subjected to centrifugal separation to remove the solid residues, thus obtaining crude extract solution. Ammonium sulfate was dissolved in this crude extract solution such that the final concentration is 30%, and stirred for 20 minutes at room temperature, thereby precipitating contaminating proteins. Precipitated proteins were removed by centrifugal separation. Further, ammonium sulfate was added thereto and dissolved such that the final concentration is 48%. The solution was stirred for 20 minutes at room temperature, thereby precipitating GDH containing fractions. The supernatant was removed by centrifugal separation, and the thus obtained GDH fractions were dissolved in 20 mL of 50 mM potassium phosphate buffer (pH 7.0). The resulting solution was applied to a Resource Q (GE Healthcare) column having a column volume of 6 mL in order to adsorb contaminating proteins in the column, and GDH was passed through the column. Ammonium sulfate was dissolved in this passed-through solution such that the final concentration is 22.8%. The resulting solution was applied to a hydrophobic Resource ISO column (GE Healthcare, volume of 6 mL), and adsorbed thereto. The adsorbed proteins were eluted with a gradient of ammonium sulfate concentration from 22.8% to 0% to collect fractions having GDH activity. The fractions were further gel filtrated using Superdex 200 as a separation column and a buffer solution of pH 7.0 containing tris (50 mM) and sodium chloride (0.15 mM) as an elution buffer. The thus obtained GDH fractions were used as the purified solution.

Example 2

Cloning of GDH Gene

The GDH solution (10 μL) obtained in Example 1 was mixed with an equal amount of 2×SDS sample buffer (10 mM Tris-HCl, 10% glycerol, 2% SDS, 0.1% bromophenol blue, 2% (v/v) 2-mercaptoethanol, pH 6.8), and the mixture was boiled at 100° C. for 10 minutes. The mixture was then applied to a 12.5% acrylamide gel, and electrophoresed at 40 mA, followed by CBB staining of the gel using CBB Stain One (NACALAI TESQUE, INC.). The main band in the sample was cut out from the stained gel, and its peptide sequence was analyzed by a mass spectrometer. Based on the thus obtained inferred amino acid sequence, degenerated PCR primers containing mixed bases were designed, and a PCR reaction was performed using genomic DNA as a template. This PCR reaction solution was applied to a 1% agarose gel for electrophoresis, and stained with ethidium bromide. Then, bands corresponding to internal fragments of GDH gene amplified under UV irradiation were cut out. Next, DNA was extracted and purified from the cut out gel pieces, using Wizard SV Gel and PCR Clean-up System (Promega KK.). Using TArget Clone Plus (TOYOBO Co., Ltd.), the obtained DNA fragments were ligated to the cloning vector pTA2 attached to the kit, according to the TA cloning method. The ligation product was added to *Escherichia coli* JM109 competent cells (TOYOBO Co., Ltd., Competent high JM109), transformed by heat shock, applied to an LB agarose plate containing 100 μg/mL of ampicillin, and cultured overnight at 37° C. to form transformed colonies. A plurality of colonies were inoculated into 5 mL of LB media (containing 100 μg/mL of ampicillin), and cultured overnight. Using Quantum Prep mini-prep kit (Bio-Rad Laboratories, Inc.), plasmids were extracted from the culture according to the manual of the kit. A partial base sequence of the intended GDH gene was determined by analyzing the base sequence of an insert of each extracted plasmid. Further, based on the determined sequence, a primer directed to the outside of the sequence of the internal region was designed. Using this primer and LA PCR in vitro Cloning Kit (TAKARA BIO INC.), the regions of the 5' and 3' ends of the GDH gene were amplified and their base sequences were determined; the entire base sequence of the gene was thereby determined. The determined base sequence is shown in SEQ. ID NO. 1, and the inferred amino acid sequence is shown in SEQ. ID NO. 2.

Example 3

Construction of GDH Expression Vector

A primer, which was designed to have a sequence with an NdeI site at the start codon and a BamHI site immediately after the stop codon of the GDH gene, was used to perform a PCR reaction with the hyperthermophile genomic DNA as a template. The reaction solution was applied to a 1% agarose gel, electrophoresed, and stained with ethidium bromide. Then, bands of GDH gene amplified under UV irradiation were cut out. Next, DNA was extracted and purified from the cut out gel pieces. Using TArget Clone Plus, the obtained DNA fragments were inserted into the cloning vector pTA2 attached to the kit (pTA2TGDH1). The following operation was carried out in order to replace the inserted NdeI site (CATATG) present inside the GDH gene with another base sequence without changing the amino acids to be encoded. Using oligo DNA having a base sequence comprising 5'-AGCACGGCATTTGGGGGCTCC-3' (SEQ. ID NO. 4) and 5'-GGAGCCCCCAAATGCCGTGCT-3' (SEQ. ID NO. 5) as a primer, a reaction similar to PCR was performed in a thermal cycler with the above-obtained pTA2TGDH1 as a template. Subsequently, DpnI, in an amount of 2% by mass relative to the reaction solution, was added thereto, and the mixture was treated at 37° C. for one hour. Thereby, the template (pTA2TGDH1) was digested. This DpnI treated solution was added to *Escherichia coli* JM109 competent cells (TOYOBO Co., Ltd., Competent high JM109), transformed by heat shock, applied to an LB agarose plate containing 100 μg/mL of ampicillin, and cultured overnight at 37° C. to form transformed colonies. A plurality of colonies were separately inoculated into 5 mL of LB media (containing 100 μg/mL of ampicillin), and cultured overnight. Using Quantum Prep mini-prep kit, plasmids were extracted from the culture. The base sequence of each plasmid thus obtained was analyzed to confirm that the codon that encodes isoleucine at position 113 in the GDH amino acid sequence was converted from ATA to ATT, i.e., A at position 339 in the GDH gene sequence was replaced by T, and the product was designated plasmid pTA2TGDH2 with the corrected sequence. This pTA2TGDH2 was subjected to restriction enzyme treatment with NdeI and BamHI, and electrophoresed in a 1% agarose gel, and gel pieces containing GDH gene (having NdeI and BamHI cut ends at the 5' and 3' ends, respectively) were cut out. Then, DNA was extracted and purified using Wizard SV Gel and PCR Clean-up System. This DNA was mixed with expression vector pET21a that had been treated with the same restriction enzyme. This mixed solution was mixed with an equal amount of Ligation High (TOYOBO Co., Ltd.) and incubated at 16° C. for 30 minutes for ligation. This ligation solution was added to *Escherichia coli* JM109 competent cells, transformed by heat shock, applied to an LB agarose plate containing 100 μg/mL of ampicillin, and cultured overnight at 37° C. to form transformed colonies. Within these transformed colonies, those that were confirmed to contain an insert by colony direct PCR were inoculated in 5 mL of LB media (containing 100 μg/mL of ampicillin), and cultured overnight. Using a plasmid extraction kit, plasmids were extracted from the microbial cells that were obtained by centrifugal separation of the culture. The sequence of the insert of each plasmid was analyzed to confirm that the plasmid contained the correct gene sequence. This plasmid was designated expression vector (pET21aTGDH2).

Example 4

GDH Gene Expression and Purification

According to the manual attached to the *Escherichia coli* BL21 (DE3) competent cells (Stratagene), the pET21aTGDH1 obtained in Example 3 was subjected to heat shock to obtain transformed strains. These transformed colonies were suspended in 5 mL of LB media (containing 100 μg/mL of ampicillin) in 8 test tubes, and cultured with shaking overnight at 37° C. The thus obtained culture was inoculated into 4 Sakaguchi flasks with a volume of 2 L containing 800 mL of LB media (with 100 μg/mL of ampicillin) such that 8 mL of the culture was inoculated in each flask. These flasks were shaken at 37° C. and 120 rpm for 3 hours. Then, IPTG was added thereto such that the final concentration is 0.1 mM when the cell turbidity reaches approximately 0.6 at 660 nm. Further, the cultivation with shaking was continued at 37° C. and 120 rpm for 4 hours. The culture was centrifugally separated using a high speed cooling centrifugal separator, and the supernatant was removed by decanting. The thus obtained microbial cells were suspended in 70 mL of 50 mM Tris-hydrochloric acid buffer solution+0.1 M NaCl (pH 8.0). This suspension was treated for 20 minutes using an ultrasonic crusher (TOMY SEIKO CO., LTD, UD-201) at output level of 4 and at a duty cycle of 40%, thereby crushing the microbial cells. The crushed cell solution was subjected to centrifugal separation to remove residue, thus obtaining crude extract solution. The thus obtained crude extract solution was treated at 85° C. for 30 minutes to denature contaminating proteins, which were then removed by centrifugal separation. The supernatant fraction was passed through the Resource Q column buffered with 50 mM Tris-HCl·0.1 M NaCl (pH 8.0), and then ammonium sulfate, in an amount of 21.3% by mass relative to the passed-through solution, was dissolved therein. This solution was adsorbed to the Resource ISO column buffered with 50 mM Tris-HCl·22.8% ammonium sulfate (pH 8.0), and gradient elution was carried out by decreasing the concentration of ammonium sulfate concentration to 0% to collect GDH fractions. These fractions were further gel filtrated using Superdex 200, and the thus obtained GDH fractions were used as the purified recombinant GDH solution. This purified solution was confirmed to be a purified product that shows a single band by CBB staining of SDS page.

Example 5

Coenzyme Concentration Dependency and Substrate Concentration Dependency of Recombinant GDH Using the GDH obtained in Example 4, the maximum reaction rate (Vmax) and the Michaelis constant (Km) of the GDH of the present invention at 60° C. and pH 8.0 were determined. The calculation method was as follows: the substrate concentration and coenzyme concentration were modified to measure activity by a method in accordance with the above-described activity measurement example, and the constants were calculated from the straight line determined by the least-squares method using double reciprocal plots. As a result, when NAD was used as a coenzyme, the Michaelis constant (Km) was 10.3 mM for NAD and 66.9 mM for glucose. The maximum reaction rate (Vmax) at a glucose concentration of 1 M was 1670 U/mg. Further, when NADP was used as a coenzyme, the Michaelis constant (Km) was 0.075 mM for NADP and 5.27 mM for glucose. The maximum reaction rate (Vmax) at a coenzyme concentration of 5 mM was 333 U/mg. From the Michaelis constant for each coenzyme, GDH of the present invention is presumed to mainly use NADP as a coenzyme for its activity in vivo; however, the maximum reaction rate is about 5 times higher when NAD is used.

Example 6

Temperature Stability of Recombinant GDH

The temperature stability was investigated using GDH obtained in Example 4. The GDH solution (dissolved in 50 mM Tris-HCl, 0.1 M, NaCl, pH 8.0) having a protein concentration of 0.17 mg/ml, was heated at a temperature in a range from 50° C. to 95° C. for 30 minutes, and the activity before heating was compared with the activity after heating. The ratio of the activity after heating relative to the activity before heating (residual activity ratio) is as shown in FIG. 1. The enzyme of the present invention showed a residual activity ratio of 96% at 90° C., and 85% at 95° C.

Example 7

Temperature Dependency of Recombinant GDH Reaction Rate

The temperature dependency of the reaction rate was investigated using the GDH obtained in Example 4. Varied reaction temperatures, 85° C., 80° C., 60° C., 37° C., and 25° C., were used to investigate the activity at each reaction temperature by a method in accordance with the above-described activity measurement example. Table 1 shows the results. The enzyme shows the highest activity at around 85° C. It was found that the enzyme shows activity even at room temperature. For example, the activity was 40 U/mg at 37° C., and 18.6 U/mg at 25° C.

TABLE 1

| Reaction Temperature (° C.) | U/mg |
|---|---|
| 85 | 978 |
| 80 | 961 |
| 60 | 313 |
| 37 | 40.0 |
| 25 | 18.6 |

TABLE 2

| Substrate | In the presence of NAD | In the presence of NADP |
|---|---|---|
| Glucose | 100 | 100 |
| Xylose | 0.1 | 2.2 |
| Galactose | >0.1 | 1.1 |
| Maltose | >0.1 | 2.4 |
| Lactose | 0.3 | 0.1 |
| Sorbitol | >0.1 | 0.2 |
| Sucrose | >0.1 | 0.2 |
| Mannose | >0.1 | 1.2 |

Example 8 pH Stability of Recombinant GDH

The pH stability was investigated using the GDH obtained in Example 4. Buffer solutions used were 0.1 M citric acid buffer (pH 4.3 to 6.2), 0.1 M potassium phosphate buffer (pH 6.1 to 8.1), 0.1 M Bicine buffer (pH 7.9 to 8.8), and 0.1 M glycine buffer (pH 8.8 to 10.6). GDH was added to each buffer solution such that the final concentration is 5 µg/mL, and the activity immediately after addition was measured. The GDH solution was further incubated at 25° C. for 24 hours, and the activity after incubation was measured. The ratio of the activity after incubation relative to the activity before incubation (residual activity ratio) is shown in FIG. 2. GDH of the present invention did not undergo a reduction in activity in the pH range of 5.8 to 9.2, and showed a residual activity ratio of 90% or higher in the pH range of 4.8 to 9.7.

Example 9 pH Dependency Recombinant of GDH Reaction Rate

The pH dependency of the reaction rate was investigated using the GDH obtained in Example 4. The activity was measured by a method in accordance with the activity measurement example. As a buffer component corresponding to Bicine in the composition of the reaction solution shown in the activity measurement example, potassium phosphate was used for pH 6.5 to 7.9, Bicine for pH 7.9 to 8.8, CHES for pH 8.6 to 9.7, and glycine for pH 9.8 to 10.2. FIG. 3 is a graph that shows the relative activity, where the activity that is the highest is assumed to be 100. The range of optimum pH for GDH of the present invention is distributed on the alkaline side. The activity was highest at pH 9.7.

Example 10

Substrate Specificity of Recombinant GDH

The reactivity of the GDH obtained in Example 4 with various sugars was investigated. The activity was measured using 5 mM of NADP or NAD as a coenzyme, and 150 mM of sugars such as glucose, xylose, galactose, maltose, lactose, sorbitol, sucrose, and mannose as the substrate in the composition of the reaction solution shown in the above-described activity measurement example. Table 2 shows the relative activity with each substrate, where the activity with glucose is assumed to be 100. When NADP was used as a coenzyme, the specific activities with xylose and maltose were about 2%, and the specific activities with galactose and mannose were about 1%, based on the specific activity with glucose. Almost no reaction was observed with lactose, sorbitol, and sucrose. On the other hand, when NAD was used as a coenzyme, the specific activities with xylose, maltose, galactose, mannose, lactose, sorbitol, and sucrose were less than 1%, based on the specific activity with glucose. Particularly in view of the reactivity of the enzyme with galactose and xylose, it was found that the enzyme has an excellent substrate specificity compared with known GDH derived from hyperthermophilic archaea.

Example 11

Potassium Ion Concentration Dependency of Recombinant GDH Reaction Rate

The potassium ion concentration dependency of the reaction rate was investigated using the GDH obtained in Example 4. GDH activity was measured using reaction solutions in which KCl at various concentrations were added to the composition of the reaction solution shown in the activity measurement example. The relative activities where the activity without KCl is assumed to be 100 were as follows: 129 at the KCl concentration of 0.1 mol/L; 133 at 0.2 mol/L; 146 at 0.5 mol/L; and 150 at 1.0 mol/L. It was found that the activity of GDH of the present invention increases along with an increase in the potassium ion concentration, and that the activity remained almost the same in the potassium ion concentration range of 0.5 mol/L or higher.

Example 12

Quantification of Glucose Using Recombinant GDH

As a reagent for glucose quantification, a solution of pH 8.0 containing the following components was prepared: 0.1 mol/L Bicine, 0.5 mol/L KCl, 20 mmol/L β-NAD, and 1 U/mL GDH (obtained in Example 4; the activity is in accordance with the above described activity measurement example). This reagent (900 µL) was placed in a quartz cell, set into an incubator-housed absorption spectrometer, and preheated at 25° C. for 5 minutes. Then, a glucose solution (15 µL) was added thereto to obtain solutions in which the final concentrations of glucose in the solution were 2, 5, 10, and 15 mmol/L, and a reaction was carried out at 25° C. for 3 minutes under each glucose concentration to monitor a change in absorbance at 340 nm. The increase in absorbance per minute was calculated from the linear portion of the absorbance change over 3 minutes, and the change in absorbance that occurred when distilled water was added instead of glucose was subtracted. The resulting values (dmAbs/minute) were plotted (FIG. 4). The glucose concentration was plotted along the horizontal axis, and the ΔmAbs/minute was plotted along the vertical axis. The locus of plotted points drew a straight line. The determination coefficient of the regression line determined by the least-squares method was: $R^2=0.9993$. It was thus confirmed that the glucose concentration can be accurately quantified using the GDH of the present invention.

INDUSTRIAL APPLICABILITY

Glucose dehydrogenase produced by the present invention can be supplied as a reagent for measuring a blood glucose level, and as a material for a blood glucose sensor and glucose quantification kit.

---

SEQUENCE LISTING

Figure 1:
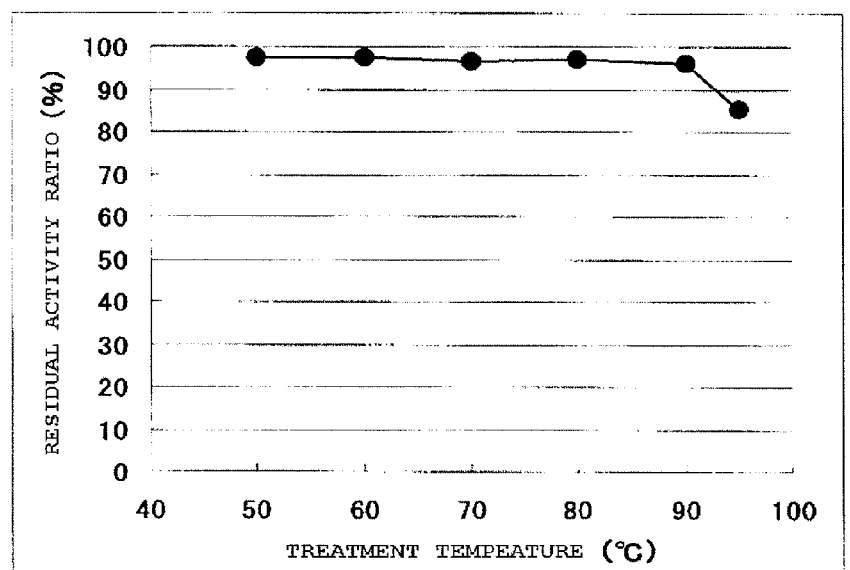
FIG. 1 shows the temperature stability of *Escherichia coli* recombinant GDH comprising an amino acid sequence identical to SEQ ID NO: 2. The vertical axis shows the residual activity ratio (relative activity after 30-minute heat treatment at each temperature, where the GDH activity before heat treatment is assumed to be 100%), and the horizontal axis shows the temperatures during heat treatment.
Figure 2:
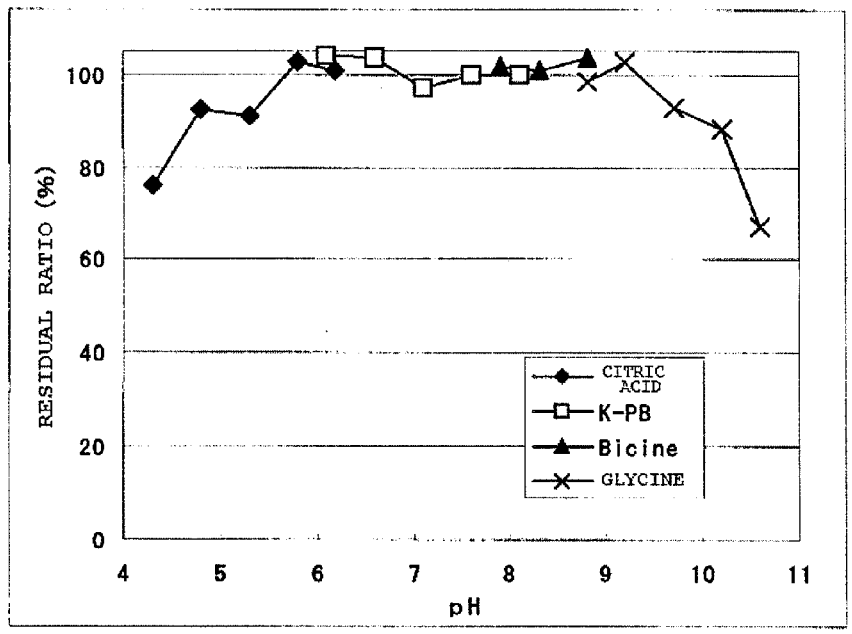
FIG. 2 shows the pH stability of *Escherichia coli* recombinant GDH comprising an amino acid sequence identical to SEQ ID NO: 2. The vertical axis shows the residual activity ratio (relative activity after heating at 25° C. for 24 hours at each pH condition, where the GDH activity before heat treatment is assumed to be 100%), and the horizontal axis shows the pH of the reaction solution. The data was obtained using 0.1 M citric acid buffer for pH 4.3 to 6.2; 0.1 M potassium phosphate buffer for pH 6.1 to 8.1; 0.1M Bicine buffer for pH 7.9 to 8.8; and 0.1 M glycine buffer for pH 8.8 to 10.6.
Figure 3:
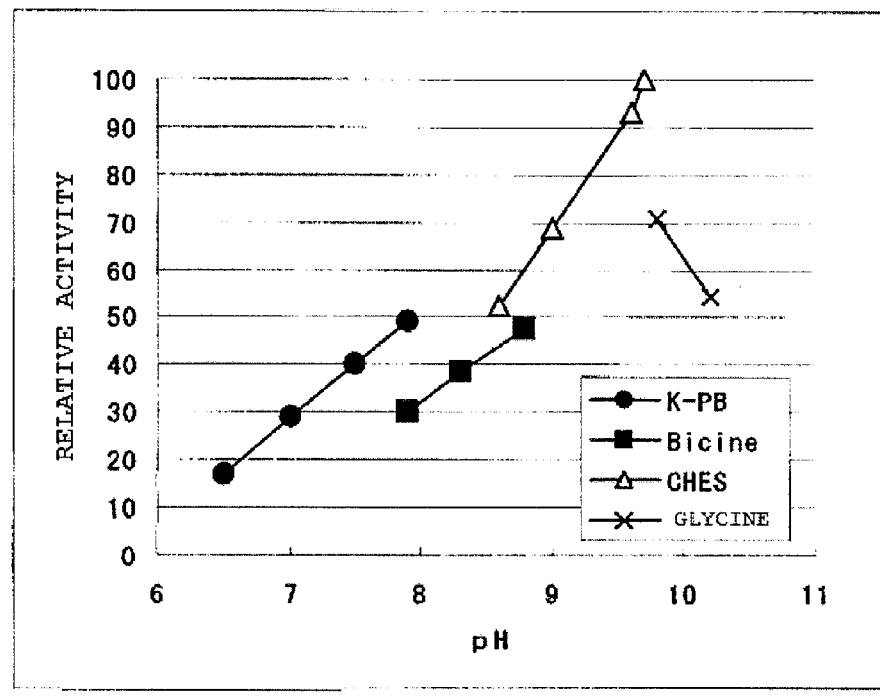
FIG. 3 shows the pH dependency of *Escherichia coli* recombinant GDH comprising an amino acid sequence identical to SEQ ID NO: 2. The vertical axis shows the relative activity (relative activity at each pH condition, where the activity that is the highest is assumed to be 100), and the horizontal axis shows the pH of the reaction solution. The data was obtained using potassium phosphate buffer for pH 6.5 to 7.9; Bicine buffer for pH 7.9 to 8.8; CHES buffer for pH 8.6 to 9.7; and glycine buffer for pH 9.8 to 10.
Figure 4:
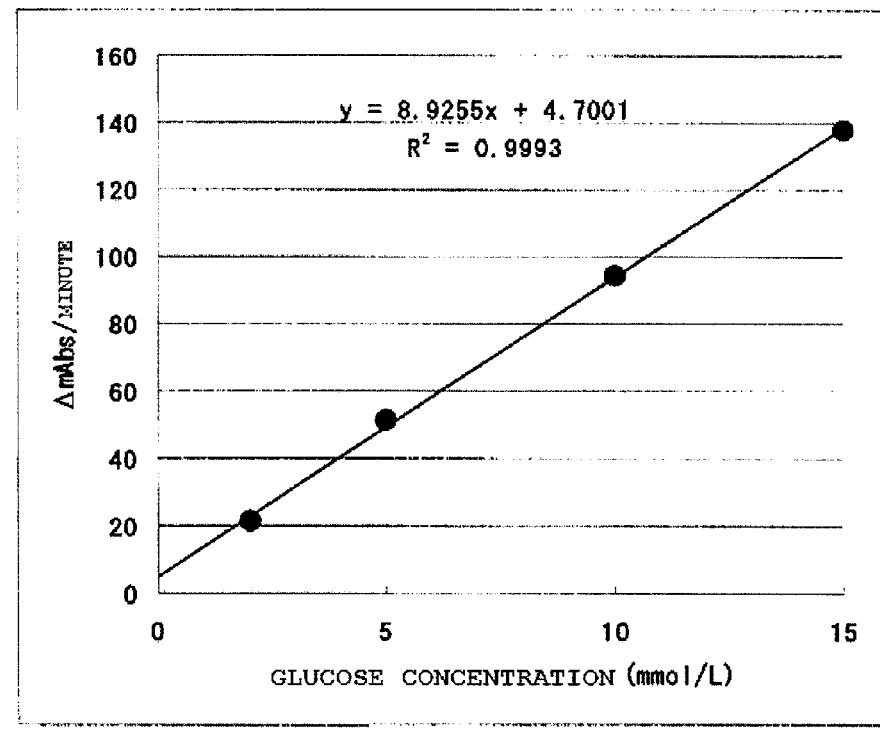
FIG. 4 shows a calibration curve prepared using a standard glucose solution for *Escherichia coli* recombinant GDH comprising an amino acid sequence identical to SEQ ID NO: 2. The vertical axis shows the rate of increase in the absorbance at 340 nm per minute (ΔmAbs/minute), and the horizontal axis shows the glucose concentration in the reaction solution

```
<160> NUMBER OF SEQ ID NOS: 5

<210> SEQ ID NO 1
<211> LENGTH: 1047
<212> TYPE: DNA
<213> ORGANISM: Thermoproteus sp. GDH1

<400> SEQUENCE: 1
atgaaggcgg taacggtcac cccaggggtg cccgagtcct taaggcttag agatgtcccc        60
aagccctcgc cgaggagagg acaggtcctc ctcaagccgt tgatggtcgg cgtttgcgga       120
actgacaagg agataatcga ggggaaatac gggaaggcgc cggagggcag cgactacctc       180
atcctcggcc acgaggccct cgccgaagtc gccgagttgg gcgacggcgt taataatgtc       240 tcggcgggggg acctcgtggt gcccacggtg aggaggcccg tgaactgcga cctcccagtg       300
gactactgcc ccgttggcaa atacgtggag cacggcatat gggggctcca cggccacgcg       360
gccgagtact cggtgaccga tgcggcgtat ctggtcaagg tcccgaagga gatagccgat       420
atagccgtgt tgaccgagcc gttgtccgtg gtggagaaag gcgtggagct aggcgttacg       480
gcctaccagt cgaggctcgg gaaaaagccc gagaccgcgt tggtgctcgg agcaggcccc       540
gtgggccttc tggcgaccat ggtgctcagg ctcatgggcc tatcggtcac caccgtggcc       600
acgcggccgc cggatagcct aaaggccaag ctggccaggg agatcggcgc tacgtatgtc       660
gacgcggcac acgagaaact gaccgggacc tacgacttgg tcgtagaggc cacccggggct       720 gtctccgtgg cgctggaagg gctcgcgagg ctcggcccgg gcggagtcga ggtgctcctc       780
ggcgtgtacc cgcccggcgg taagctagaa gacgcgggga gcctcctcac cgacgccgtg       840
ttgaacaaca agctcgtcgt cggctcggtc aacgccggct tgaggcactt cgaggcgcg       900 ttgagacact tgaaggaggc caaggacaag ttcggggatt ggccgaagaa gctgatcacg       960
aagacggcca ctctcgacaa ctaccaagag gcctattcct ggacccacga ggatataaag      1020
acggttctag tgctacaaca cttataa                                          1047

<210> SEQ ID NO 2
<211> LENGTH: 348
<212> TYPE: PRT
<213> ORGANISM: Thermoproteus sp. GDH1

<400> SEQUENCE: 2

Met Lys Ala Val Thr Val Thr Pro Gly Val Pro Glu Ser Leu Arg Leu
1               5                   10                  15

Arg Asp Val Pro Lys Pro Ser Pro Arg Arg Gly Gln Val Leu Leu Lys
            20                  25                  30
```

```
Pro Leu Met Val Gly Val Cys Gly Thr Asp Lys Glu Ile Ile Glu Gly
        35                  40                  45
Lys Tyr Gly Lys Ala Pro Glu Gly Ser Asp Tyr Leu Ile Leu Gly His
 50                  55                  60
Glu Ala Leu Ala Glu Val Ala Glu Leu Gly Asp Gly Val Asn Asn Val
 65                  70                  75                  80
Ser Ala Gly Asp Leu Val Val Pro Thr Val Arg Arg Pro Val Asn Cys
                 85                  90                  95
Asp Leu Pro Val Asp Tyr Cys Pro Val Gly Lys Tyr Val Glu His Gly
                100                 105                 110
Ile Trp Gly Leu His Gly His Ala Ala Glu Tyr Ser Val Thr Asp Ala
            115                 120                 125
Ala Tyr Leu Val Lys Val Pro Lys Glu Ile Ala Asp Ile Ala Val Leu
        130                 135                 140
Thr Glu Pro Leu Ser Val Val Glu Lys Gly Val Glu Leu Gly Val Thr
145                 150                 155                 160
Ala Tyr Gln Ser Arg Leu Gly Lys Lys Pro Glu Thr Ala Leu Val Leu
                165                 170                 175
Gly Ala Gly Pro Val Gly Leu Leu Ala Thr Met Val Leu Arg Leu Met
            180                 185                 190
Gly Leu Ser Val Thr Thr Val Ala Thr Arg Pro Pro Asp Ser Leu Lys
        195                 200                 205
Ala Lys Leu Ala Arg Glu Ile Gly Ala Thr Tyr Val Asp Ala Ala His
210                 215                 220
Glu Lys Leu Thr Gly Thr Tyr Asp Leu Val Val Glu Ala Thr Gly Ala
225                 230                 235                 240
Val Ser Val Ala Leu Glu Gly Leu Ala Arg Leu Gly Pro Gly Gly Val
                245                 250                 255
Glu Val Leu Leu Gly Val Tyr Pro Pro Gly Gly Lys Leu Glu Asp Ala
            260                 265                 270
Gly Ser Leu Leu Thr Asp Ala Val Leu Asn Asn Lys Leu Val Val Gly
        275                 280                 285
Ser Val Asn Ala Gly Leu Arg His Phe Glu Ala Ala Leu Arg His Leu
290                 295                 300
Lys Glu Ala Lys Asp Lys Phe Gly Asp Trp Pro Lys Lys Leu Ile Thr
305                 310                 315                 320
Lys Thr Ala Thr Leu Asp Asn Tyr Gln Glu Ala Tyr Ser Trp Thr His
                325                 330                 335
Glu Asp Ile Lys Thr Val Leu Val Leu Gln His Leu
            340                 345

<210> SEQ ID NO 3
<211> LENGTH: 2133
<212> TYPE: DNA
<213> ORGANISM: Thermoproteus sp. GDH1

<400> SEQUENCE: 3
ttagggctaa gcccatgcga gtcgcgcgcc cggggcgccg ggcgcggcgc acggctcagt      60
aacacgtgcc caacctaacc tcgggagggg acaaccccg ggaaactggg gctgatcccc      120
catagcggaa gggcgctgga aggccccttc ccccaaaggg acctcgggcg atctcccgag     180
gtccgcccga gggtgggggc acggcctatc aggtagttgg cggggtaacg gccgccaag      240 ccgaagacgg gtaggggcgg tgagagccgt gagccccgag atgggcactg agacaagggc     300
ccaggcccta cggggtgcag caggcgcgaa tactccgcaa tgcgggcaac cgcgacgggg     360
```

```
ccaccccgag tgccgggcga agagcccggc ttttgcccgg tgtaaggagc cgggcgaata    420 agcgggggt  aagtctggtg tcagccgccg cggtaatacc agccccgcga gtggtcaggg    480
tgattactgg gcttaaagcg cccgtagccg gcccggcaag tcgctcctga aatccccggg    540
ctcaacccgg gggctggggg cgatactgcc gggctagggg cgggagagg  ccgccggtac    600 tccgggggta ggggcgaaat cctataatcc ccggaggacc accagtggcg aaagcgggcg    660
gccagaacgc gcccgacggt gaggggcgaa agcgggggga gcaaagggga ttagataccc    720
ctgtagtccc ggccgtaaac gatgcgggct agctgtcggc cgggcttagg gcccggccgg    780
tggcgtaggg aaaccgttaa gcccgccgcc tgggagtac  ggccgcaagg ctgaaactta    840
aaggaattgg cgggggggca ccacaagggg tgaagcttgc ggcttaattg gagtcaacgc    900
cggaaacctt acccggggcg acagcaggat gaaggccagg ctaacgacct tgccggacga    960
gctgagagga ggtgcatggc cgtcgtcagc tcgtgccgtg aggtgtccgg ttaagtccgg   1020
caacgagcga gaccccccacc cctagttgct tccccgctct tcggggcggg gggcacacta   1080
gggggactgc cggcgtaagc cggaggaagg aggggggccac ggcaggtcag tataggggcc   1140
tatccgtaag gagggccccg ctgaggcccc gaaagccgtg gccccaggt  agggtattta   1200 ttccagaaca tgaagatctg ggactacctc tgcggtttag tggcggcaga tgggcatcta   1260
gacgaggatg gctatgtaac catatcccaa aaagataaga gatttatcga gaggattata   1320
gagttattaa aataggctgg tgtgcagata aactcagttt tttacgataa aggagcaggc   1380
gtttggaaga taaaagtcaa ggacgacgtc ttctatcact atttggtcga aacggcgta    1440 ccgcccggcc gaaaagcccg ttgcataaag ccgccaagtc ccgcagtaga tccgatgtgg   1500
tatatagcag gttttataga cggagacggc tgggtggaac aagtagtgaa gaccgtgaag   1560
ggcaagaggt actactacat acgggtaggc ctgaaaacca agagcagaga gctgagggac   1620
tggatcttac aagccctggc cgacctgggc attagggcca acaaggctga cgagaaagac   1680
ggatacgaga tccacatcga cagcgtagat gcatggcgcc taatcctcct tctccagaat   1740
ccatcccata cggagaaggc caggtcggcc agggacgata ggctctagtc ttcctccaag   1800
ccctacctgg ggccgcggcc gggagacccc ggggctgcac gcgagctgca atggcgggga   1860
cagcgggatc cgaccccgaa aggggaggc  aatcccgtaa accccgcccc agtagggatc   1920
gagggctgca actcgccctc gtgaacgtgg aatcccctagt aaccgcgtgt caccaacgcg   1980
cggtgaatac gtccctgccc cttgcacaca ccgcccgtcg caccacccga ggggttctc    2040 tgcgaggccc ctcgcttggg gcaacccagg tgggggacg  agcagagaac ccccgagggg   2100
ggtgaagtcg taacaaggta gccgtagggg aaa                               2133
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic sequence

<400> SEQUENCE: 4
agcacggcat ttgggggctc c                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 5
ggagccccca aatgccgtgc t                                                    21
```

The invention claimed is:

1. An isolated glucose dehydrogenase comprising an amino acid sequence with 90% or more identity to the amino acid sequence of SEQ ID NO: 2, wherein the glucose dehydrogenase has a reactivity of less than 3% with respect to maltose, galactose, and xylose, based on its reactivity with glucose, and has a temperature stability of 80° C. or more.

2. The glucose dehydrogenase according to claim 1, wherein the glucose dehydrogenase utilizes nicotinamide adenine dinucleotide (NAD) or nicotinamide adenine dinucleotide phosphate (NADP) as a coenzyme in a glucose oxidation reaction.

3. An isolated glucose dehydrogenase comprising an amino acid sequence with 90% or more identity to the amino acid sequence of SEQ ID NO: 2, wherein the glucose dehydrogenase is from a hyperthermophilic archaeon, and wherein the glucose dehydrogenase has the following properties (A) to (F):
- (A) temperature stability: 90° C. or less;
- (B) pH stability: 4.8 to 9.7;
- (C) optimum reaction temperature: 85° C.;
- (D) optimum pH: 9.7;
- (E) coenzyme: nicotinamide adenine dinucleotide (NAD) or nicotinamide adenine dinucleotide phosphate (NADP);
- (F) substrate specificity: when NADP is utilized as the coenzyme, the glucose dehydrogenase exhibits an activity of 2% or more and less than 3% upon xylose and maltose, based on its activity upon glucose, an activity of 1% or more and less than 2% upon galactose and mannose, based on its activity upon glucose, and an activity of less than 1% upon lactose, sorbitol, and sucrose, based on its activity upon glucose; and
when NAD is used as the coenzyme, the glucose dehydrogenase exhibits an activity of less than 1% upon xylose, maltose, galactose, mannose, lactose, sorbitol, and sucrose, based on its activity upon glucose.

4. An isolated glucose dehydrogenase having the amino acid sequence shown in SEQ ID NO. 2.

5. An isolated glucose dehydrogenase comprising an amino acid sequence with 90% or more identity to the amino acid sequence of SEQ ID NO: 2, wherein the glucose dehydrogenase has the following properties (A) to (F):
- (A) temperature stability: 90° C. or less;
- (B) pH stability: 4.8 to 9.7;
- (C) optimum reaction temperature: 85° C.;
- (D) optimum pH: 9.7;
- (E) coenzyme: nicotinamide adenine dinucleotide (NAD) or nicotinamide adenine dinucleotide phosphate (NADP);
- (F) substrate specificity: when NADP is utilized as the coenzyme, the isolated glucose dehydrogenase exhibits an activity of 2% or more and less than 3% upon xylose and maltose, based on its activity upon glucose, an activity of 1% or more and less than 2% upon galactose and mannose, based on its activity upon glucose, and an activity of less than 1% upon lactose, sorbitol, and sucrose, based on its activity upon glucose; and
when NAD is used as the coenzyme, the isolated glucose dehydrogenase exhibits an activity of less than 1% upon xylose, maltose, galactose, mannose, lactose, sorbitol, and sucrose, based on its activity upon glucose.

6. An isolated DNA encoding the glucose dehydrogenase recited in claim 1.

7. An expression vector comprising the DNA recited in claim 6, the DNA being functionally coupled to a promoter operable in a host cell to which the DNA is introduced.

8. A transformed microorganism transformed using the expression vector recited in claim 7.

9. The transformed microorganism according to claim 8, wherein the microorganism is *Escherichia coli*.

10. A method for producing glucose dehydrogenase comprising culturing the microorganism recited in claim 8, and collecting glucose dehydrogenase from the resulting culture.

11. A composition for quantifying glucose, comprising the glucose dehydrogenase recited recited in claim 1.

12. A method for quantifying glucose, comprising obtaining a sample containing glucose and adding the glucose dehydrogenase recited in claim 1 to the sample.

13. An isolated DNA encoding the glucose dehydrogenase recited in claim 4.

14. An expression vector comprising the DNA recited in claim 13, the DNA being functionally coupled to a promoter operable in a host cell to which the DNA is introduced.

15. A transfoimed microorganism transformed using the expression vector recited in claim 14.

16. The transformed microorganism according to claim 15, wherein the microorganism is *Escherichia coli*.

17. A method for producing glucose dehydrogenase comprising culturing the microorganism recited in claim 15, and collecting glucose dehydrogenase from the resulting culture.

18. A composition for quantifying glucose, comprising the glucose dehydrogenase recited in claim 4.

19. A method for quantifying glucose, comprising obtaining a sample containing glucose and adding the glucose dehydrogenase recited in claim 4 to the sample.

* * * * *